(12) United States Patent
Meunier et al.

(10) Patent No.: US 11,311,848 B2
(45) Date of Patent: Apr. 26, 2022

(54) BLADELESS MIXER

(71) Applicants: CENTRE NATIONAL DE LA RECHERCHE SCIENTIFIQUE (CNRS), Paris (FR); UNIVERSITE D'AIX MARSEILLE, Marseilles (FR); ECOLE CENTRALE DE MARSEILLE, Marseilles (FR)

(72) Inventors: Patrice Meunier, Plan de Cuques (FR); Richard Manasseh, Melbourne (AU)

(73) Assignees: CENTRE NATIONAL DE LA RECHERCHE SCIENTIFIQUE (CNRS), Paris (FR); UNIVERSITE DAIX MARSEILLE, Marseilles (FR); ECOLE CENTRALE DE MARSEILLE, Marseilles (FR)

( * ) Notice: Subject to any disclaimer, the term of this patent is extended or adjusted under 35 U.S.C. 154(b) by 723 days.

(21) Appl. No.: 16/081,318

(22) PCT Filed: Mar. 1, 2017

(86) PCT No.: PCT/EP2017/054813
§ 371 (c)(1),
(2) Date: Aug. 30, 2018

(87) PCT Pub. No.: WO2017/149034
PCT Pub. Date: Sep. 8, 2017

(65) Prior Publication Data
US 2021/0187453 A1 Jun. 24, 2021

(30) Foreign Application Priority Data

Mar. 1, 2016 (FR) ..................................... 1651703

(51) Int. Cl.
*B01F 29/62* (2022.01)
*B01F 29/00* (2022.01)
(Continued)

(52) U.S. Cl.
CPC ........ *B01F 29/62* (2022.01); *B01F 29/40111* (2022.01); *B01F 29/40112* (2022.01);
(Continued)

(58) Field of Classification Search
CPC .......... B01F 9/04; B01F 9/0043; B01F 9/004; B01F 9/0038; B01F 2215/0431;
(Continued)

(56) References Cited

U.S. PATENT DOCUMENTS 3,219,322 A * 11/1965 Murer ....................... C21C 5/32
366/220
3,277,540 A * 10/1966 Buhrer ..................... B01F 9/02
366/180.1
(Continued)

FOREIGN PATENT DOCUMENTS

EP 1 374 991 A1 1/2004
EP 2 893 973 A1 7/2015
(Continued)

OTHER PUBLICATIONS

International Search Report as issued in International Patent Application No. PCT/EP2017/054813, dated May 31, 2017.

*Primary Examiner* — Charles Cooley
(74) *Attorney, Agent, or Firm* — Pillsbury Winthrop Shaw Pittman LLP

(57) ABSTRACT

A bladeless mixer for mixing a liquid, includes a cylindrical or truncated cone-shaped receptacle having an axis A and a radius R, the radius R being the shortest distance between the axis A and a side wall of the receptacle, the liquid to be mixed being placed in the receptacle and having an exposed surface at a height H measured along axis A; a member for tilting the receptacle such that axis A forms a non-zero-degree angle of up to 30° relative to the vertical direction; a member for imparting a rotational movement to the recep- (Continued)

tacle along axis A at an angular speed of rotation $\Omega$; wherein the aspect ratio H/R of the height H to the radius R and the angular speed of rotation $\Omega$ are selected such that an inherent mode of inertia of the liquid has an unstable resonance when the receptacle is tilted and rotates.

4 Claims, 2 Drawing Sheets

(51) Int. Cl.
  *B01F 101/44* (2022.01)
  *C12M 3/04* (2006.01)
(52) U.S. Cl.
  CPC ....... *B01F 29/40114* (2022.01); *C12M 27/10* (2013.01); *B01F 29/4033* (2022.01); *B01F 2101/44* (2022.01); *B01F 2215/0422* (2013.01); *B01F 2215/0431* (2013.01); *B01F 2215/0481* (2013.01)
(58) Field of Classification Search
  CPC ...... B01F 2009/0063; B01F 2215/0073; B01F 2215/0422; B01F 2215/0481; B01F 9/0001; B01F 2009/0065; B01F 29/62; B01F 29/40111; B01F 29/40112; B01F 29/40114; B01F 29/4033; B01F 2101/44; B01F 29/40113; C12M 27/10
  See application file for complete search history.

(56) References Cited

U.S. PATENT DOCUMENTS

| | | | |
|---|---|---|---|
| 4,435,082 A | 3/1984 | Bishop | |
| 2021/0187453 A1* | 6/2021 | Meunier | ................... B01F 9/04 |

FOREIGN PATENT DOCUMENTS

| | | | | |
|---|---|---|---|---|
| FR | 1 362 354 A | | 5/1964 | |
| FR | 3048367 A1 * | | 9/2017 | ................ B01F 9/04 |
| GB | 2 258 176 A | | 2/1993 | |

* cited by examiner

US 11,311,848 B2

BLADELESS MIXER

CROSS-REFERENCE TO RELATED APPLICATIONS

This is the U.S. National Stage of PCT/EP2017/054813, filed Mar. 1, 2017, which in turn claims priority to French Patent Application No. 1651703, filed Mar. 1, 2016, the entire contents of all applications are incorporated herein by reference in their entireties.

TECHNICAL FIELD OF THE INVENTION

The technical field of the invention is that of mixers. The present invention concerns a bladeless mixer and a mixing method.

TECHNOLOGICAL BACKGROUND OF THE INVENTION

To mix a liquid it is known to use a mixer with a rotating blade. However, the rotating blade creates a high shear within the liquid, by delamination of the boundary layer. Use of a blade also generally requires the said blade to be cleaned regularly, and makes it difficult, or impossible, to guarantee that the liquid to be mixed will not be contaminated due to the said blade.

The problem of high shear is known in particular in the field of biotechnology, and for example in the field of cell culture in solution in a bioreactor. The cultivated cells require a regular supply of oxygen, and regular evacuation of the carbon dioxide which they emit. Oxygen is supplied and the carbon dioxide evacuated typically by means of a rotating blade. But the high shear created by the rotating blade can kill the cultivated cells, which prefer a relatively stationary medium.

To be able to mix a liquid whilst avoiding use of a blade, it is known to inject air bubbles in the lower part of a tank containing the liquid to be mixed. Such a solution does, in particular, have the disadvantage that it requires an air bubble injection device. There are also applications in which the injection of air bubbles is contra-indicated.

A device is therefore sought enabling a liquid to be mixed with a low shear rate within the liquid, and a low risk of contamination of the liquid, whilst avoiding the use of a complex air bubble injection device.

SUMMARY OF THE INVENTION

The invention provides a solution to the above-mentioned problems, by proposing a bladeless device to mix a liquid without injection of air bubbles.

One aspect of the invention concerns a bladeless mixer in order to mix a liquid, comprising:
- a cylindrical or tapered container of axis A and radius R, where radius R is the smallest distance between axis A of the container and a side wall of the container, where the liquid to be mixed is placed in the container, and where it has a free surface of height H measured along axis A;
- a device to tilt the container such that axis A forms a non-zero angle $\alpha$, chosen to be less than or equal to 30° relative to vertical;
- a device to drive the container with a rotational motion around axis A, at an angular speed of rotation $\Omega$;
- aspect ratio H/R of height H over radius R and angular speed of rotation $\Omega$ are chosen so as to observe an unstable resonance of an inertial eigenmode of the liquid to be mixed when the container is tilted and rotating.

In the present document the expression "cylindrical container" is understood to mean a container having a side wall defined by a straight line called the generator, passing through a variable point describing a curve, called the guide curve, which maintains a fixed direction. The expression "roughly cylindrical container" is understood to mean a cylindrical or tapered container. Indeed, the diametrical variations of the container's section do not disrupt operation of the mixer if they are kept small. It will be understood that manufacture of the container can produce shapes which are not perfectly cylindrical, and in particular tapered shapes. The expression "liquid to be mixed" is understood to mean a liquid and at least one species to be mixed; for example, the species to be mixed can be a second liquid and/or a passive scalar which does not influence the flow properties of the liquid, such as a colourant or a dissolved gas, such as $CO_2$ or $O_2$ dissolved in an aqueous solution.

In the present document "radius R of the roughly cylindrical container of axis A" is the smallest distance between axis A of the container and a side wall of the container.

An inertial eigenmode can generally be defined as a global motion of a rotating liquid, where the motion is:
- periodic or stationary over time,
- sinusoidal according to azimuth angle $\theta$, and
- forced by a disturbance of the liquid.

The expression "azimuth angle $\theta$" is understood to mean the angle enabling the position of a point to be identified using cylindrical coordinates. FIG. 1c shows diagrammatically a point M of cylindrical coordinates (r, $\theta$, z).

The expression "the motion is sinusoidal according to azimuth angle $\theta$" is understood to mean that, at every point of the liquid which is not constrained by a wall of the container, each component of the speed is expressed as $\sin(m\theta)$, where m is the azimuth wavenumber.

The inertial eigenmodes of azimuth wavenumber m=1 are advantageously forced by tilting the rotating container such that axis A forms angle $\alpha$ relative to vertical.

Aspect ratio H/R of height H over radius R is chosen such that a resonance of one of the said inertial eigenmodes is achieved. Powerful and large motion then occurs in the volume of the resonating liquid, producing effective mixing with very low shear.

Angular speed of rotation $\Omega$ of the container is chosen such that an unstable resonance of the inertial eigenmode of the liquid placed in the tilted, rotating container is achieved. The expression "unstable" is understood to mean that other motions, different from the motion of the inertial eigenmode, appear within the liquid, without any additional external constraint.

Mixing within the liquid is indeed better when the resonance is unstable. The presence of an unstable resonance of an inertial eigenmode in a fluid can be checked, in particular, by making the dynamic currents appear within the fluid. To accomplish this one can, typically, add mica flakes to the liquid to be mixed, and then illuminate these flakes by means of a vertical laser layer directed along the axis of the cylinder. By this means it is possible to display the spatial flow structure, and therefore check for the presence of an unstable resonance of an inertial eigenmode. An unstable resonance of an inertial eigenmode causes characteristic unsteady structures to appear, the brightness of which oscillates rapidly close to the edge of the container. The expression "unsteady structure" is understood to mean a structure which is unstable over time.

Another aspect of the invention concerns a method of mixing a liquid by means of a bladeless mixer containing a cylindrical or tapered container of axis A and radius R, where R is the smallest distance between axis A of the container and a side wall of the container, a device to tilt the container such that axis A forms a non-zero angle $\alpha$, chosen such that it is less than or equal to 30° relative to vertical, and a device to drive the container, where the method includes the following steps:

a) placing the liquid in the container such that it has a free surface at a height H measured along axis A;
b) applying a rotational motion to the container around axis A, with an angular speed of rotation $\Omega$, where aspect ratio H/R of height H over radius R and angular rotational speed $\Omega$ are chosen so as to observe an unstable resonance of an inertial eigenmode of the liquid.

In addition to the characteristics which have just been mentioned in the previous paragraph, the bladeless mixer according to one aspect of the invention or the mixing method may each have one or more additional characteristics, from among the following, considered individually or in all technically possible combinations:

In a first embodiment aspect ratio H/R of height H over radius R is advantageously chosen such that:

$$1,79 \times k \leq \frac{H}{R} \leq 2,19 \times k$$

where k is a non-zero natural integer. This facilitates the appearance of a resonance of the first inertial eigenmode. Natural integer k is preferentially equal to 1.

According to the first embodiment, and for k=1, angular speed of rotation $\Omega$ is chosen such that:

$$\frac{\Omega \times R^2 \times \alpha}{\nu} > 1000$$

for which formula $$\frac{\Omega \times R^2}{\nu}$$

is equal to the Reynolds number
according to one embodiment according to the invention:

$$\frac{\Omega \times R^2 \times \alpha}{\nu} > 3000$$

where $\alpha$ is less than or equal to 2°
according to another embodiment according to the invention:

$$\frac{\Omega \times R^2 \times \alpha}{\nu} > 5000$$

where $\alpha$ is between 3° and 7°
where $\Omega$ is the angular speed of rotation expressed in rad/s, R the radius of the container expressed in m, $\alpha$ the angle of tilt between axis A and vertical, expressed in degrees °, and $\nu$ the kinematic viscosity of the liquid to be mixed, expressed in m²/s. This facilitates an unstable resonance of the first inertial eigenmode. According to one embodiment of the invention, $\Omega$ is constant.

In a second embodiment aspect ratio H/R of height H over radius R is advantageously chosen such that:

$$0,86 \times k \leq \frac{H}{R} \leq 1,06 \times k$$

where k is a non-zero natural integer. This facilitates the appearance of a resonance of the second inertial eigenmode. Natural integer k is preferentially equal to 1.

According to the second embodiment, and for k=1, angular speed of rotation $\Omega$ is chosen such that:

$$\frac{\Omega \times R^2 \times \alpha}{\nu} > 15000$$

and $\alpha$ is between 5° and 10°
according to another embodiment, $$\frac{\Omega \times R^2 \times \alpha}{\nu} > 30000$$

and $\alpha$ is less than or equal to 5°
where $\Omega$ is the angular speed of rotation expressed in rad/s, R the radius of the container expressed in m, $\alpha$ the angle of tilt between axis A and vertical, expressed in degrees °, and $\nu$ the kinematic viscosity of the liquid to be mixed, expressed in m²/s. This facilitates an unstable resonance of the second inertial eigenmode. According to one embodiment of the invention, $\Omega$ is constant.

In a third embodiment aspect ratio H/R of height H over radius R is advantageously chosen such that:

$$0,56 \times k \leq \frac{H}{R} \leq 0,68 \times k$$

where k is a non-zero natural integer. This facilitates the appearance of a resonance of the third inertial eigenmode. Natural integer k is preferentially equal to 1.

According to the third embodiment, and for k=1, angular speed of rotation $\Omega$ is chosen such that:

$$\frac{\Omega \times R^2 \times \alpha}{\nu} > 50000$$

where $\Omega$ is the angular speed of rotation expressed in rad/s, R the radius of the container expressed in m, $\alpha$ the angle of tilt between axis A and vertical, expressed in degrees °, and $\nu$ the kinematic viscosity of the liquid to be mixed, expressed in m²/s.

This facilitates an unstable resonance of the third inertial eigenmode. According to one embodiment of the invention, $\Omega$ is constant.

According to a particular embodiment of the invention, an unstable resonance of an inertial eigenmode can be facilitated by varying angular speed of rotation Ω, with a variation of angular speed of rotation Ω which is preferentially less than or equal to 25% during a complete revolution of the container.

The invention and its various applications will be better understood on reading the description which follows, and on examining the figures which accompany it.

BRIEF DESCRIPTION OF THE FIGURES

The figures are given for information only, and are not restrictive of the invention in any manner.

DETAILED DESCRIPTION OF AT LEAST ONE EMBODIMENT OF THE INVENTION

Unless otherwise stipulated, a given element shown in different figures has a single reference.

Figure 1A:
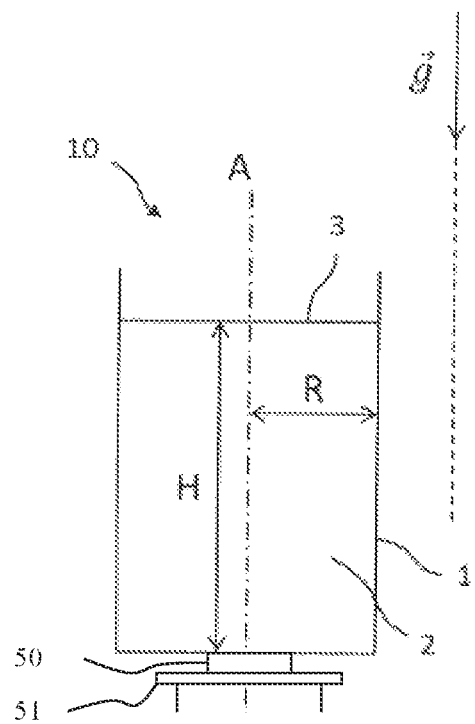
FIG. 1a shows diagrammatically a bladeless mixer according to an embodiment of the invention in an idle position.
Figure 1B:
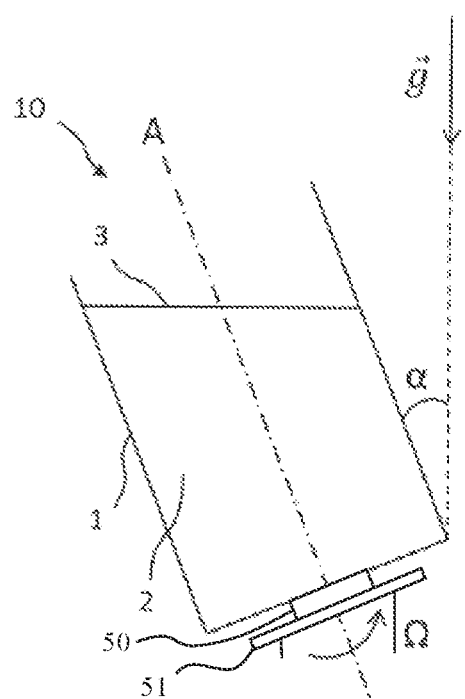
FIG. 1b shows diagrammatically the bladeless mixer of FIG. 1a in an operating position.
Figure 1C:
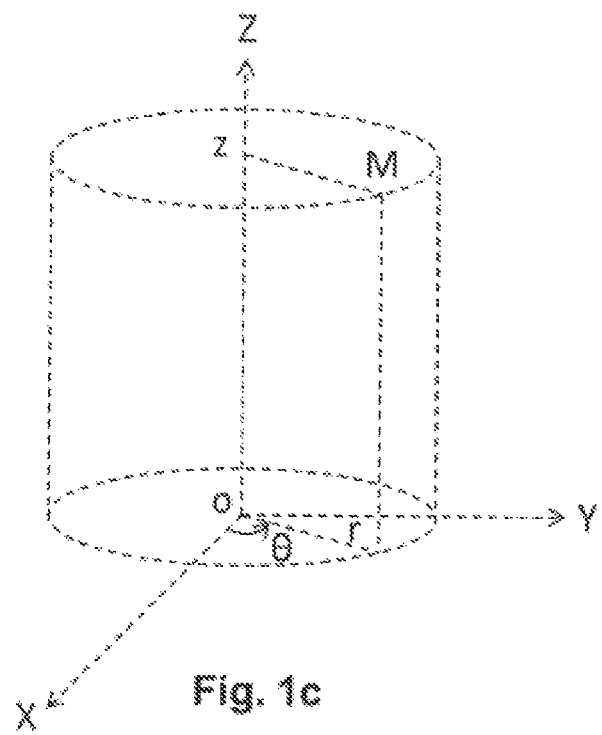
FIG. 1c shows diagrammatically a system of cylindrical coordinates.

FIG. 1a shows diagrammatically a bladeless mixer 10 according to an embodiment of the invention in an idle position. FIG. 1b shows diagrammatically bladeless mixer 10 in an operating position. FIGS. 1a and 1b are described jointly.

Mixer 10 contains a roughly cylindrical container 1, of axis A and of radius R. A liquid to be mixed 2 is placed in container 1. Liquid to be mixed 2 is characterised by a kinematic viscosity ν, typically expressed in m$^2$/s. Liquid to be mixed 2 has a free surface 3 at a height H measured along axis A. Free surface 3 is, by definition, the surface of the liquid to be mixed 2 which is not in contact with the walls of container 1. Height H can be defined as the length of axis A which is immersed in liquid 2. Height H is typically measured in the idle position of FIG. 1a. Height H and radius R are typically expressed in m.

In the idle position of FIG. 1a axis A of container 1 has a vertical direction, and container 1 is stationary. The expression "vertical direction" is understood to mean a direction parallel to the direction of force of gravity g.

In the operating position of FIG. 1b container 1 is tilted and rotating around axis A. Container 1 is tilted by means of a tilting device 51. The tilt is chosen such that axis A of container 1 forms a non-zero angle α which is less than or equal to 30° relative to the vertical direction, angle α is preferentially less than or equal to 15°, and more preferentially less than or equal to 5°. Angle α can, for example, be equal to 0.5°, or to 1°, or to 5°, or to 15°. With an angle α higher than 30°, the flow on the free surface may produce shear. Container 1 is rotated around axis A by a drive device 50. Container 1 is made to rotate around axis A with an angular speed of rotation Ω typically expressed in rad/s.

Aspect ratio H/R of height H over radius R is advantageously chosen such that a resonance of an inertial eigenmode of liquid to be mixed 2 is achieved. A first inertial eigenmode can be defined as a global and periodic or stationary disrupting motion, which disturbs liquid to be mixed 2 placed in container 1 which is tilted and rotating. The tilt of axis A relative to vertical enables rotating liquid 2 to be forced into an inertial eigenmode. For each inertial eigenmode there is a plurality of resonances.

For the first inertial eigenmode of liquid 2 placed in container 1 which is tilted and rotating, aspect ratio H/R is chosen such that:

$$1,79 \times k \leq \frac{H}{R} \leq 2,19 \times k$$

where k is a non-zero natural integer, and k is preferentially equal to 1. Aspect ratio H/R is preferentially chosen such that it is roughly equal to 1.99. This helps facilitate the appearance of a resonance of the first inertial eigenmode.

For the second inertial eigenmode of liquid 2 placed in container 1 which is tilted and rotating, aspect ratio H/R is advantageously chosen such that:

$$0,86 \times k \leq \frac{H}{R} \leq 1,06 \times k$$

where k is a non-zero natural integer, and k is preferentially equal to 1. Preferentially, aspect ratio H/R is chosen to be roughly equal to 0.96. This helps facilitate the appearance of a resonance of the second inertial eigenmode.

For the third inertial eigenmode of liquid 2 placed in container 1 which is tilted and rotating, aspect ratio H/R is advantageously chosen such that:

$$0,56 \times k \leq \frac{H}{R} \leq 0,68 \times k$$

where k is a non-zero natural integer, and k is preferentially equal to 1. Aspect ratio H/R is preferentially chosen to be roughly equal to 0.62. This helps facilitate the appearance of a resonance of the third inertial eigenmode.

Angular speed of rotation Ω of container 1 is advantageously chosen such that an unstable resonance of the inertial eigenmode of liquid 2 placed in tilted, rotating container 1 is achieved. The expression "unstable" is understood to mean that other motions, different from the motion of the inertial eigenmode, appear within liquid 2, without any additional external constraint. Mixing within liquid 2 is indeed better when the resonance is unstable.

For the first inertial eigenmode, where k=1, and for a constant angular speed of rotation Ω, an unstable resonance of the inertial eigenmode of liquid 2 placed in container 1 which is tilted and rotating is typically observed, on the following condition:

$$\frac{\Omega \times R^2 \times \alpha}{v} > 1000$$

where:
- Ω is the angular speed of rotation expressed in rad/s,
- R is the radius of container 1 expressed in m,
- α is the angle of tilt between axis A and the vertical direction expressed in degrees
- v is the kinematic viscosity of liquid to be mixed 2, expressed in m²/s in the case of miscible liquids; kinematic viscosity is the average viscosity of the liquids.

For the second inertial eigenmode, where k=1, and for a constant angular speed of rotation Ω, an unstable resonance of the inertial eigenmode of liquid 2 placed in container 1 which is tilted and rotating is typically observed, on the following condition:

$$\frac{\Omega \times R^2 \times \alpha}{v} > 15000$$

For the third inertial eigenmode, where k=1, and for a constant angular speed of rotation Ω, an unstable resonance of the inertial eigenmode of liquid 2 placed in container 1 which is tilted and rotating is typically observed, on the following condition:

$$\frac{\Omega \times R^2 \times \alpha}{v} > 50000$$

Where radius R, angle of tilt α and kinematic viscosity v are fixed, the previous inequalities enable an assessment to be made of minimum angular speed of rotation Ω which must be applied to container 1 to create an unstable resonance, in each of the first, second and third inertial eigenmodes. In general terms, the greater angular speed of rotation Ω, the higher the rate of shear within liquid to be mixed 2, and the greater the quantity of energy required to rotate container 1. It is therefore typically sought to create an unstable resonance, whilst choosing the lowest possible angular speed of rotation Ω.

Alternatively, angular speed of rotation Ω can be variable. A variation of angular speed of rotation Ω of less than or equal to 25% during a complete revolution of container 1 is preferred.

In the present document the expression "cylindrical container" is understood to mean a container having a side wall defined by a straight line called the generator, passing through a variable point describing a curve, called the guide curve, and maintaining a constant direction. The guide curve is preferentially a circle. This container shape is preferred, since it facilitates forecasting of the flow of a liquid placed in the said container, where the container is tilted and rotating, and the definition of aspect ratio H/R, enabling a resonance of a first inertial eigenmode of the said liquid to be obtained.

Alternatively, the guide curve can be:
- an ellipse, or
- a convex polygon contained in a circle, or
- a convex polygon contained in an ellipse, or However, when a liquid is placed in a tilted, rotating container, where the container has a polygonal section, the liquid generally has a flow including vortices in the corners, which is undesirable, since a vortex dissipates large amounts of energy.

In general terms, the expression "radius of the cylindrical container of axis A" is understood to mean the smallest distance between axis A of the container and a side wall of the recipient.

Figure 2A:
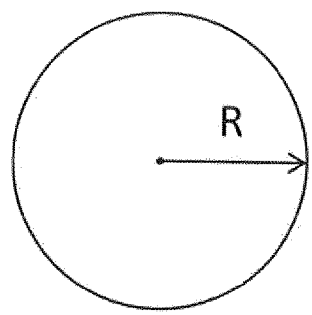
FIG. 2a shows diagrammatically a section view of a first cylindrical container of a bladeless mixer according to one embodiment of the invention.

FIG. 2a shows a section view of a first cylindrical container according to one aspect of the invention, having a guide curve in the shape of a circle. The cross-section is made using a plane perpendicular to the axis of rotation of the first cylindrical container.

Figure 2B:
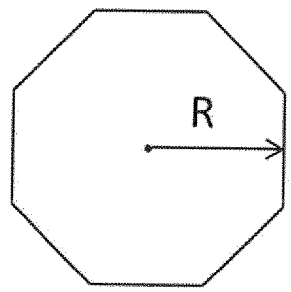
FIG. 2b shows diagrammatically a section view of a second cylindrical container of a bladeless mixer according to one embodiment of the invention.

FIG. 2b shows a section view of a second cylindrical container according to one aspect of the invention, having a guide curve in the shape of a convex N-sided polygon contained in a circle. The cross-section is made using a plane perpendicular to the axis of rotation of the second cylindrical container. In the particular example of FIG. 2b the guide curve is a regular convex octagon and N=8. Other values of N could of course be chosen, such as N=4 or N=16. The largest possible value of N is chosen in preference, in order that the guide curve approaches the circle containing the N-sided convex polygon.

Figure 3A:
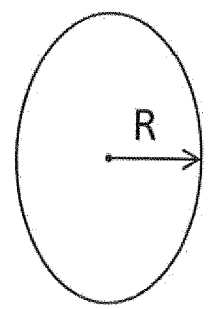
FIG. 3a shows diagrammatically a section view of a third cylindrical container of a bladeless mixer according to one embodiment of the invention.

FIG. 3a shows a section view of a third cylindrical container according to one aspect of the invention, having a guide curve in the shape of an ellipse. The cross-section is made using a plane perpendicular to the axis of rotation of the third cylindrical container. An ellipse in which the foci are as close to one another as possible is preferentially chosen, in order that the guide curve approaches a circle.

Figure 3B:
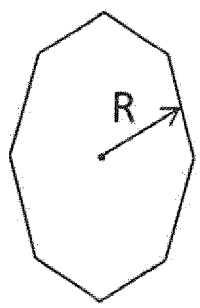
FIG. 3b shows diagrammatically a section view of a fourth cylindrical container of a bladeless mixer according to one embodiment of the invention.

FIG. 3b shows a section view of a fourth cylindrical container according to one aspect of the invention, having a guide curve in the shape of a convex N-sided polygon contained in an ellipse. The foci of the ellipse containing the N-sided convex polygon are preferentially as close as possible to one another. The cross-section is made using a plane perpendicular to the axis of rotation of the fourth cylindrical container. In the particular example of FIG. 3b the guide curve is a regular convex octagon contained within an ellipse and N=8. Other values of N could of course be chosen, such as N=4 or N=16. The largest possible value of N is chosen in preference, in order that the guide curve approaches the ellipse containing the N-sided convex polygon.

The expression "roughly cylindrical container" is understood to mean a cylindrical or tapered container. Indeed, the diametrical variations of the container's section do not disrupt the mixer's operation if they are kept small, i.e. less than or equal to 20%, and preferentially less than or equal to 10%.

It will be understood that the manufacture of the container can lead to shapes which are not perfectly cylindrical, in particular tapered shapes.

Figure 4A:
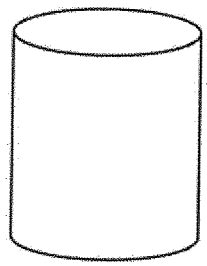
FIG. 4a shows diagrammatically a first perspective view of a roughly cylindrical container of a bladeless mixer according to one embodiment of the invention.

FIG. 4a shows diagrammatically a first perspective view of a roughly cylindrical container according to one aspect of the invention: the dimensions of the section of the container in a plane perpendicular to its axis of rotation are constant, and the container is perfectly cylindrical.

Figure 4B:
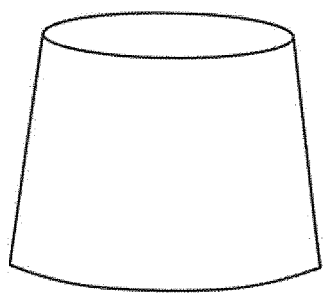
FIG. 4b shows diagrammatically a second perspective view of a roughly cylindrical container of a bladeless mixer according to one embodiment of the invention.

FIG. 4b shows diagrammatically a second perspective view of a roughly cylindrical container according to one aspect of the invention: the dimensions of the section of the container in a plane perpendicular to its axis of rotation vary continuously; the container is tapered. The container of FIG. 4b has a base and an aperture, and the radius of the base is higher than the radius of the aperture.

Figure 4C:
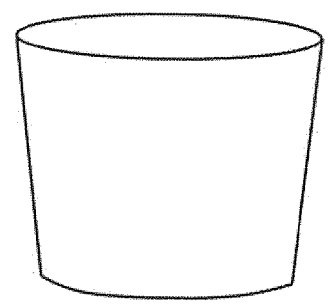
FIG. 4c shows diagrammatically a third perspective view of a roughly cylindrical container of a bladeless mixer according to one embodiment of the invention.

FIG. 4c shows diagrammatically a third perspective view of a roughly cylindrical container according to one aspect of the invention: the dimensions of the section of the container in a plane perpendicular to its axis of rotation vary continuously; the container is tapered. The container of FIG. 4c has a base and an aperture, and the radius of the base is lower than the radius of the aperture.

FIGS. 4a to 4c show three examples of roughly cylindrical containers according to one aspect of the invention, where each container has a circular guide curve. In accordance with the description given above in connection with FIGS. 2a, 2b, 3a and 3b, it will be understood that the examples of FIGS. 4a to 4c can be extended to containers with elliptical guide curves, or guide curves with the shape of a convex polygon contained in a circle, or with the shape of a convex polygon contained in an ellipse.

The invention claimed is:

1. A method of mixing a liquid by means of a bladeless mixer containing a cylindrical or tapered container of axis A and radius R, wherein R is the smallest distance between axis A of the container and a side wall of the container, the container being tiltable such that axis A forms a non-zero angle α, chosen such that the angle is less than or equal to 30° relative to vertical, and the container being rotatable, the method comprising:
   a) placing the liquid in the container such that the liquid has a free surface at a height H measured along axis A when axis A is vertical, and
   b) applying a rotational motion to the container around axis A, with an angular speed of rotation Ω, and applying the non-zero angle α to tilt the container, wherein an aspect ratio H/R of height H over radius R and angular rotational speed Ω are chosen so as to observe an unstable resonance of an inertial eigenmode of the liquid
wherein the inertial eigenmode of the liquid is
   the first mode with 1.79≤H/R≤2.19 and (Ω×R²×α)/v>1000, or
   the second mode with 0.86≤H/R≤1.06 and (Ω×R²×α)/v>15000 or
   the third mode with 0.56≤H/R≤0.68 and (Ω×R²×α)/v>50000
wherein Ω is the angular speed of rotation expressed in rad/s, R is the radius of the container expressed in m, H the height of the liquid in meter measured along axis A; α the angle of tilt between axis A and vertical, expressed in degrees °, and v the kinematic viscosity of the liquid to be mixed, expressed in m²/s.

2. The method according to claim 1, wherein the angular speed of rotation Ω is chosen such that:

$$\frac{\Omega \times R^2 \times \alpha}{v} > 3000$$

and α is less than or equal to 2° or $$\frac{\Omega \times R^2 \times \alpha}{v} > 5000$$

and α is between 3° and 7°.

3. The method according to claim 1, wherein the angular speed of rotation Ω is chosen such that:

$$\frac{\Omega \times R^2 \times \alpha}{v} > 15000$$

where α is between 5 and 10° or $$\frac{\Omega \times R^2 \times \alpha}{v} > 30000$$

where α is less than or equal to 5°.

4. The method according to claim 1, wherein:
   the angular speed of rotation Ω is variable, and
   the variation of angular speed of rotation Ω is less than or equal to 25% during a complete revolution of the container.

* * * * *